(12) United States Patent
Ciccognani et al.

(10) Patent No.: US 9,987,209 B2
(45) Date of Patent: Jun. 5, 2018

(54) MULTI-FUNCTIONAL COMPOSITION FOR COSMETIC FORMULATIONS

(71) Applicant: Arch Chemicals, Inc., Atlanta, GA (US)

(72) Inventors: Diana Ciccognani, Cumming, GA (US); Falen D. Lockett, Alpharetta, GA (US); Laura Szymczak, Wall, NJ (US)

(73) Assignee: Arch Chemicals, Inc., Atlanta, GA (US)

( * ) Notice: Subject to any disclaimer, the term of this patent is extended or adjusted under 35 U.S.C. 154(b) by 0 days. days.

(21) Appl. No.: 14/248,750

(22) Filed: Apr. 9, 2014

(65) Prior Publication Data

US 2014/0301964 A1 Oct. 9, 2014

Related U.S. Application Data

(60) Provisional application No. 61/810,012, filed on Apr. 9, 2013.

(51) Int. Cl.

| | |
|---|---|
| *A61K 8/36* | (2006.01) |
| *A61K 8/37* | (2006.01) |
| *A61K 8/33* | (2006.01) |
| *A61K 8/34* | (2006.01) |
| *A61K 8/365* | (2006.01) |
| *A61Q 17/00* | (2006.01) |
| *A61K 8/39* | (2006.01) |
| *A61Q 19/00* | (2006.01) |
| *A61Q 1/14* | (2006.01) |
| *A61Q 5/12* | (2006.01) |
| *A61Q 5/02* | (2006.01) |
| *A61Q 1/10* | (2006.01) |

(52) U.S. Cl.
CPC ............. *A61K 8/37* (2013.01); *A61K 8/33* (2013.01); *A61K 8/345* (2013.01); *A61K 8/347* (2013.01); *A61K 8/361* (2013.01); *A61K 8/365* (2013.01); *A61K 8/39* (2013.01); *A61Q 17/005* (2013.01); *A61Q 1/10* (2013.01); *A61Q 1/14* (2013.01); *A61Q 5/02* (2013.01); *A61Q 5/12* (2013.01); *A61Q 19/00* (2013.01)

(58) Field of Classification Search
None
See application file for complete search history.

(56) References Cited

U.S. PATENT DOCUMENTS

| | | |
|---|---|---|
| 3,714,356 A | 1/1973 | Burrous et al. |
| 3,887,701 A | 6/1975 | Nachtigal |
| 4,201,765 A | 5/1980 | Sichak |
| 5,670,160 A | 9/1997 | Eggensperger et al. |
| 6,086,903 A | 7/2000 | Trinh et al. |
| 8,338,361 B2 | 12/2012 | Takahashi et al. |
| 2003/0176508 A1 | 9/2003 | Cheetham et al. |
| 2004/0253194 A1 | 12/2004 | Rioux et al. |
| 2006/0057175 A1 | 3/2006 | Ciccognani et al. |
| 2006/0258559 A1 | 11/2006 | Tanaka et al. |
| 2008/0233064 A1 | 9/2008 | Tabakman et al. |
| 2008/0260659 A1 | 10/2008 | Natsch |
| 2009/0208427 A1 | 8/2009 | Ishida et al. |
| 2010/0310494 A1 | 12/2010 | Sundaresan |
| 2011/0086918 A1 | 4/2011 | Ciccognani et al. |
| 2011/0152384 A1 | 6/2011 | Gunn et al. |
| 2011/0230560 A1* | 9/2011 | Piva et al. ............ 514/568 |
| 2012/0251460 A1 | 10/2012 | Dalko |
| 2012/0282356 A1 | 11/2012 | Schrader et al. |
| 2013/0045954 A1 | 2/2013 | De Leij et al. |

FOREIGN PATENT DOCUMENTS

| | | | |
|---|---|---|---|
| EP | 1882471 | 1/2008 | |
| JP | 2006 036731 | 2/2006 | |
| WO | WO-9611572 A1 * | 4/1996 | ............ A01N 31/02 |
| WO | WO 2011/095372 | 8/2011 | |

OTHER PUBLICATIONS http://cosmetictestlabs.com/natural_vs_synthetic_cosmetic_preservatives.html archived on Nov. 1, 2012.*
https://www.ewg.org/skindeep/ingredient/701534/COCO-CAPRYLATE%3B%3B_CAPRATE/ referenced on Dec. 19, 2016.*
https://www.ewg.org/skindeep/ingredient/701053/CAPRYLIC_ACID/ referenced on Dec. 19, 2016.*
https://www.ewg.org/skindeep/ingredient/706311/STEARIC_ACID/ referenced on Dec. 19, 2016.*
International Search Report and Written Opinion for PCT/US2014/033419, dated Nov. 5, 2014.
Polyglycerois Product Data Sheet, Solvay Chemicals International, 10 pages.
Polyaldo™ Polyglycerol Esters, Product Sheets, Lonza Inc.

* cited by examiner

*Primary Examiner* — Jessica Worsham

(74) *Attorney, Agent, or Firm* — Dority & Manning, P.A.

(57) ABSTRACT

A composition is described that may be used in personal care products. The composition can serve as a preservative. In addition or alternatively, the composition may serve as a fragrance and/or as a coloring agent. The composition can contain an active compound, an organic acid, a solvent, and optionally a dispersant. In one embodiment, the active compound and the organic acid comprise all natural ingredients.

25 Claims, No Drawings

MULTI-FUNCTIONAL COMPOSITION FOR COSMETIC FORMULATIONS

RELATED APPLICATIONS

The present application is based upon and claims priority to U.S. Provisional Patent Application Ser. No. 61/810,012, filed on Apr. 9, 2013, which is incorporated herein by reference.

BACKGROUND

Preservatives have wide applications in fields like personal care, industrial, health and hygiene, pharmaceutical and wood protection. Preservatives can be a single agent or a blend of multiple agents.

Ideally, a preservative has broad-spectrum activity against all types of microorganisms at various pH levels. The preservative should also have high efficacy so that a minimum amount of the preservative can be used to save cost and to avoid or reduce any possible adverse effects caused by the preservative. Also, it is desirable that the preservative is stable to any changes in temperature encountered during manufacturing, packaging, and shipping as well as during storage of the preservative. Further, an ideal preservative is physically and chemically compatible with ingredients of different application systems so that one preservative can suitably be incorporated in various products.

In the past, various different preservatives and preservative blends have been suggested. Many preservatives in the past have comprised synthetic chemicals, meaning chemicals that do not occur naturally in nature and must be synthesized in a manufacturing facility. For many personal care products, such as cosmetic compositions, however, recent emphasis has been placed on making the compositions from naturally occurring materials. Thus, there is a need in the art for a preservative or preservative blend that is all or substantially all natural and that can replace and eliminate traditional synthetic preservative systems.

A need also exists for a preservative or preservative blend that can provide other useful properties to the composition in which it is incorporated.

SUMMARY

The present disclosure is generally directed to a composition for use in personal care products that has at least one function and, in one embodiment, displays multiple functions. In one embodiment, for instance, the composition may serve as a preservative or function to protect the personal care product. In addition to being a preservative or a protective additive, the composition can also serve as a fragrance. In still another embodiment, the composition can be used as a coloring agent for providing a personal care product with an aesthetically pleasing pink color. Of particular advantage, the composition can be made entirely or primarily from natural ingredients. As used herein, a "natural" ingredient refers to an ingredient that is derived from natural sources and can be differentiated from artificial ingredients and synthetic chemicals.

In one embodiment, the present disclosure is directed to a multi-functional composition. The multi-functional composition comprises an organic acid, a solvent, optionally a dispersant, and an active compound having the following formula:

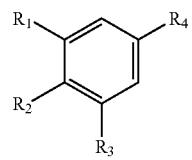

wherein:
$R_1$ and $R_2$ are H or OH;
$R_3$ comprises H, OH, or $OR_5$;
$R_4$ comprises $R_6COOR_7$; $COOR_7$; or $R_8C=O$;
$R_5$ is an alkyl group;
$R_6$ is an alkyl or alkenyl group;
$R_7$ is H, an alkyl group or an alkenyl group; and
$R_8$ is H, an alkyl group or an alkenyl group.

For instance, in one embodiment, the active compound may comprise one of the following or mixtures thereof:

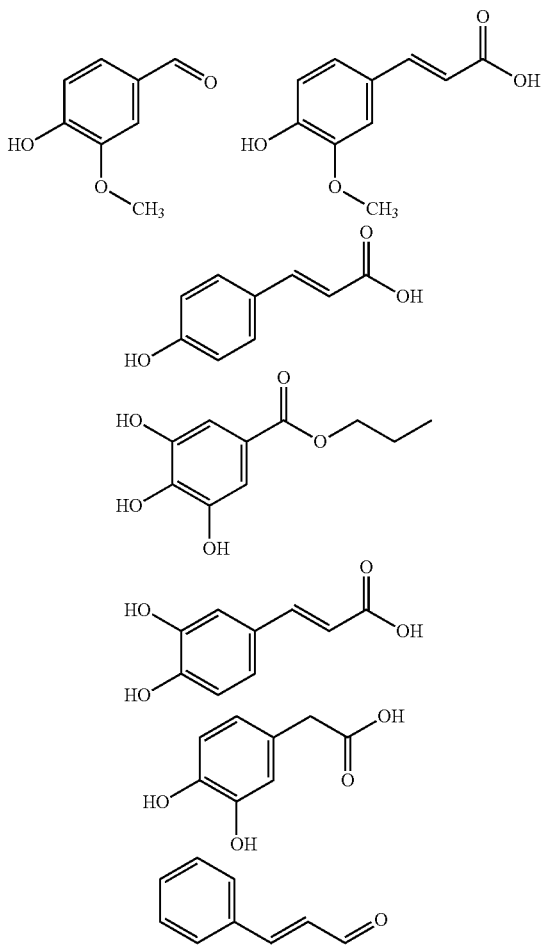

The active compound and the organic acid may work together to provide antimicrobial properties. The organic acid may comprise an organic acid having a carbon chain length of from about 1 carbon atoms to about 28 carbon atoms, such as from about 3 carbon atoms to about 18 carbon atoms. In one embodiment, the organic acid comprises octanoic acid. The active compound and the organic acid can be present in the composition at a ratio of from about 3:1 to about 20:1, such as from about 5:1 to about 15:1, such as from about 5:1 to about 10:1.

The solvent may comprise a diol, such as propanediol. In other embodiments, the solvent may comprise other alkane dials. For instance, the solvent may comprise butanediol, hexanediol, heptanediol, or pentanediol. In one particular embodiment, the solvent comprises 1,5 pentanediol, 1,4-butanediol, 2,3-butanediol, or mixtures thereof. The dispersant, on the other hand, may comprise a polyglycerol ester. In one embodiment, the active compound can be present in the composition in an amount from about 15% to about 30% by weight, such as from about 20% to about 30% by weight. The organic acid may be present in an amount from about 0.5% to about 10% by weight, such as from about 0.5% to about 5% by weight. The solvent may be present in an amount from about 40% to about 80% by weight. When present, the dispersant can be included in the composition in an amount from about 5% to about 40% by weight, such as in an amount from about 15% to about 35% by weight.

The multifunctional composition can be incorporated into any suitable personal care product. For instance, the preservative composition of the present disclosure may be contained in a personal care product in an amount from about 0.1% to about 5% by weight, such as from about 0.5% to about 3% by weight. The personal care product can comprise, for instance, any cosmetic product such as makeup remover, mascara, and the like. The personal care product may also comprise a shampoo, a conditioner, a lotion, or the like. The personal care product may contain a base composition that is combined with the multifunctional composition. The ingredients of the base composition can vary depending upon the end use of the product. The base composition may contain, for instance, surfactants, emulsifiers, water, and the like.

Other features and aspects of the present disclosure are discussed in greater detail below.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to a composition for personal care products that can be formulated to be multi-functional. In one embodiment, for instance, the composition may serve as a preservative when combined with a personal care product. In an alternative embodiment, the composition may function as a fragrance. In an additional alternative embodiment, the composition can serve as a preservative and as a fragrance. In still another embodiment, the composition can serve as a preservative, a fragrance, and as a coloring agent.

The composition of the present disclosure can provide numerous benefits and advantages. As indicated above, the composition may provide a personal care product with antimicrobial stability. In addition, the composition can also provide a pleasing fragrance. Of particular advantage, the composition can be formulated so as to be made exclusively or mostly from all natural ingredients. In this regard, the composition can replace more traditional synthetic preservative systems. When functioning as a preservative, the composition has displayed a wide variety of antimicrobial activity against numerous bacteria and fungi.

In one embodiment, the composition of the present disclosure includes an organic acid, a solvent, optionally a dispersant, and an active compound. The active compound can be naturally occurring and can generally have the following formula:

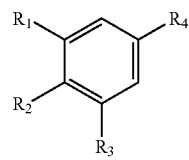

wherein:
$R_1$ and $R_2$ are H or OH;
$R_3$ comprises H, OH, or $OR_5$;
$R_4$ comprises $R_8COOR_7$; $COOR_7$; or $R_8C=O$;
$R_5$ is an alkyl group;
$R_6$ is an alkyl or alkenyl group;
$R_7$ is H, an alkyl group or an alkenyl group; and
$R_8$ is H, an alkyl group or an alkenyl group.

In one embodiment, $R_3$ terminates with a carboxylic acid group (COOH). In an alternative embodiment, $R_4$ terminates with an aldehyde group.

The active compound, for instance, may comprise one or more of the following:

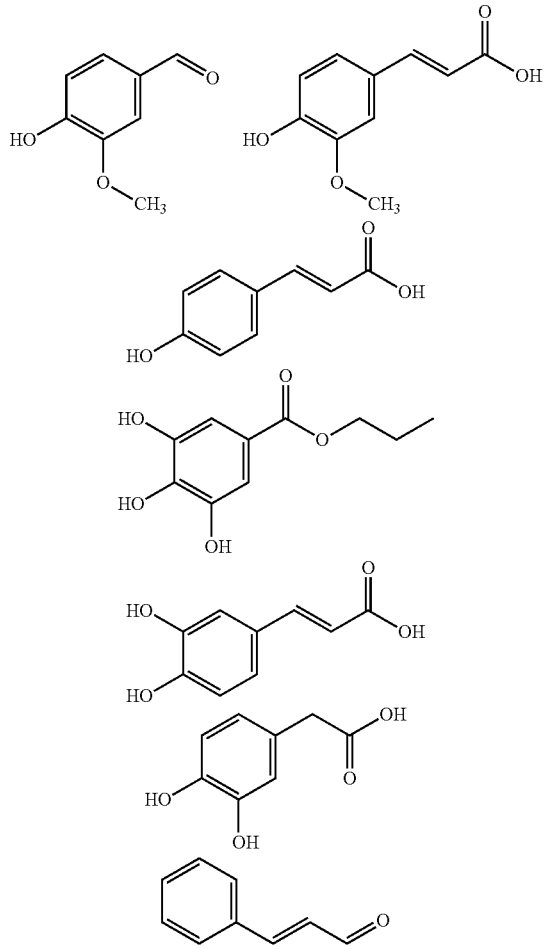

Examples of active compounds that may be used in accordance with the present disclosure include vanillin, ferulic acid, p-hydroxycinnamic acid, propyl gallate, caffeic acid, 3,4-dihydroxyphenylacetic acid, cinnamaldehyde, and mixtures thereof.

The active compound is present in the composition in an amount from about 15% to about 30% by weight, such as in an amount from about 20% to about 30% by weight. The actual amount can vary depending upon the particular active compound and the desired result. When the composition of the present disclosure is incorporated into a personal care product, the active compound is present in the personal care product in an amount generally less than 5% by weight. For instance, the active compound can be present in the personal care product at a concentration of from about 500 ppm to about 5,000 ppm, such as from about 1,000 ppm to about 2,500 ppm.

In accordance with the present disclosure, the active compound can be combined with an organic acid. It has been discovered that an organic acid can enhance the antimicrobial activity of the composition when present with the active compound. For example, when present in controlled ratios, the combination of an organic acid and an active compound as described above produces a synergy that not only improves the antimicrobial efficiency of the composition but also expands the number of microorganisms for which the composition has efficacy. In general, the ratio of the active compound to the organic acid can be from about 3:1 to about 20:1, such as from about 5:1 to about 15:1, such as from about 5:1 to about 10:1 within the composition of the present disclosure that is later added to a personal care product.

In general, any suitable organic acid may be used that may provide antimicrobial activity when combined with the active compound. In one embodiment, the organic acid may comprise an organic acid having a carbon chain length of from about 1 carbon atom to about 28 carbon atoms, such as from about 3 carbon atoms to about 18 carbon atoms. In one embodiment, the organic acid may comprise a carboxylic fatty acid. The organic acid may be derived from both natural and synthetic sources including fully hydrogenated animal and vegetable fats or oils, or from the oxidation of petroleum wax. In one embodiment, the organic acid comprises a natural ingredient.

Particularly preferred organic acids for use in the composition are saturated, linear aliphatic fatty acids with low to medium molecular weight. The more preferred organic acids for use in the present disclosure are monocarboxylic acids and dicarboxylic, hydroxyl-hydrocarbon aliphatic and aromatic moieties having 4 to 12 carbon atoms in a molecule selected from group of butyric acid, caprylic acid, capric acid, lauric acid, hexanoic acid, octanoic acid, oxalic acid, glutaric acid, malonic acid, malic acid, tartaric acid, succinic acid, lactic acid, glycolic acid, phthalic acid, benzoic acid, hydroxybenzoic acid, paraphthalic acid, metaphthalic acid, adipic acid, sebacic acid, and mixtures thereof.

In general, the organic acid can be present in the composition in an amount from about 0.5% to about 10% by weight, such as in an amount from about 0.5% to about 5% by weight.

In one embodiment, the composition may also contain a solvent. The solvent can be used either as a carrier or for dissolving or otherwise dispersing the active compound. For instance, in one embodiment, the active compound may comprise a solid that dissolves in the solvent. A solvent can be selected that not only dissolves the active compound, but also is compatible with the organic acid.

In general, any suitable solvent may be used. In one embodiment, however, the solvent comprises a natural ingredient. For instance, the solvent may comprise an alcohol, such as a did that is derived from natural sources. In one embodiment, for instance, the solvent may comprise 1,3-propanediol. Propanediol can be obtained from the fermentation of corn sugar.

In other embodiments, the solvent may comprise pentanediol, butanediol, hexanediol, heptanediol, or mixtures thereof. For instance, the solvent may comprise 1,5 pentanediol, 1,4-butanediol, 2,3-butanediol, or mixtures thereof.

When present, the amount of solvent contained in the composition can vary widely depending upon various factors including the solubility of the other ingredients. In general, the solvent can be present in the composition in an amount from about 40% to about 80% by weight.

Optionally, the composition can also contain a dispersant. A dispersant may be used in order to stabilize the formulation. A dispersant may also serve as a solubilizer for the active compound within the solvent. In one embodiment, the dispersant may also serve as an emulsifier.

Various different dispersants may be used in accordance with the present disclosure. As with the other ingredients, preferred dispersants comprise natural ingredients. In one embodiment, for instance, the dispersant may comprise a polyglycerol ester. In addition to polyglycerol esters, various other non-ionic surfactants may also be used as the dispersant, particularly if the material can be obtained from natural sources.

In one embodiment, the dispersant comprises a polyglycerol ester of a fatty acid. In general, the polyglycerol ester can contain an average of from about two glycerol groups per molecule to about 15 glycerol groups per molecule, such as from about three glycerol groups per molecule to about 12 glycerol groups per molecule, such as from about six glycerol groups per molecule to about 12 glycerol groups per molecule. In one embodiment, a polyglycerol-10 ester is used.

The fatty acid that is combined with the polyglycerol may comprise any suitable fatty acid that has a chain length of from about one carbon atom to about 28 carbon atoms, such as from about three carbon atoms to about 24 carbon atoms. In fact, any of the organic fatty acids described above may be used to produce the polyglycerol ester. Examples of polyglycerol esters that may be used as a dispersant include polyglycerol-10 oleate, polyglycerol-10 caprylate, polyglycerol-10 caprate, and mixtures thereof.

When present in the composition, the dispersant may be included in an amount from about 5% to about 40% by weight, such as in an amount from about 15% to about 35% by weight.

In one particular embodiment, the composition of the present disclosure comprises vanillin as the active compound in an amount from about 15% to about 25% by weight, octanoic acid as the organic acid in an amount from about 1% to about 3.5% by weight, 1,5 pentanediol, 1,4-butanediol, 2,3-butanediol, or 1,3 propanediol as the solvent in an amount from about 40% to about 60% by weight, and a polyglycerol ester as a dispersant in an amount of from about 25% to about 30% by weight.

As described above, the composition of the present disclosure can provide numerous advantages and benefits. The composition, for instance, can be added to a personal care product as a preservative. In one embodiment, the composition can serve as a preservative while being made entirely from natural ingredients.

In other embodiments, the composition may be added to a personal care product for various other reasons. For instance, the composition can also provide scent to a personal care product and thus serve as a fragrance. In still another embodiment, the composition may comprise a coloring agent. For instance, when combined with well-known ingredients, such as emulsifiers, for personal care products, the composition may provide the personal care product with an overall aesthetically pleasing pink color. A pink color may be highly preferred by consumers for many cosmetic products and other personal care products. In still another embodiment, the composition may serve as an antioxidant. The composition of the present disclosure may be combined with a personal care product for one or more of the above functions.

In general, the composition of the present disclosure can be incorporated into any suitable personal care product. For instance, the personal care product may comprise a cosmetic formulation, such as a face cream, makeup remover, or mascara. The personal care product may also comprise shampoo, a conditioner, or a skin lotion. The personal care product may comprise any product for topical application to a user's skin or hair. When combined with the personal care product as a preservative, the composition has effective broad spectrum preservation activity over a broad pH range. For instance, the pH of the composition and/or of the personal care product can be generally greater than about 4 and less than about 8.5, such as from 5 to about 8, such as from about 5 to about 7.

The personal care product generally comprises a base composition to which the composition of the present disclosure is added. The base composition may contain numerous and different ingredients depending upon the end use application. The personal care product, for instance, may contain solvents, surfactants, emulsifiers, consistency factors, conditioners, emollients, skin caring ingredients, moisturizers, thickeners, lubricants, fillers, anti-oxidants, other preservatives, active ingredients, in particular dermatologically active ingredients, fragrances and the like, as well as mixtures thereof. Active ingredients as mentioned herein comprise, for example, anti-inflammatories, anti-bacterials, anti-fungals and the like agents. Active ingredients suited for topical applications are particularly preferred.

Suitable surfactants comprise: alkyl sulfates e.g. sodium lauryl sulfate, ammonium lauryl sulfate; sodium cetearyl sulfate; alkyl sulfoacetates e.g. sodium lauryl sulfoacetate; alkyl ether sulfates e.g. sodium laureth sulfate; sodium trideceth sulfate; sodium oleth sulfate; ammonium laureth sulfate; alkyl ether sulfosuccinates e.g. disodium laureth sulfosuccinate; alkyl glycosides e.g. decyl glucoside; lauryl glucoside; alkyl isethionates amphoterics e.g. cocamidopropyl betaine; sodium cocoamphoacetate; sodium lauroamphoacetate; disodium lauroamphodiacetate; disodium cocoamphodiacetate; sodium lauroamphopripionate; disodium lauroamphodipropionate; potassium or ammonium salts of the aforementioned amphoterics; capryl/capramidopropyl betaine; undecylenamidopropyl betaine; lauromidopropyl betaine; and fatty alcohol polyglycol ethers.

Suitable emulsifiers are e.g. anionics as salts of fatty acids e.g. sodium stearate or sodium palmitate, organic soaps e.g. mono-, di- or triethanolaminoeate, sulfated or sulfonated compounds e.g. sodium lauryl sulfate or sodium cetyl sulfonate, saponines, lamepones; cationics as quaternary ammonium salts; nonionics as fatty alcohols, fatty acid ester with saturated or unsaturated fatty acids, polyoxyethylenesters or polyoxyethylenethers of fatty acids, polymers from ethylene oxide and propylene oxide or propylene glycol, amphotherics as phosphatides, proteins as gelatine, casein alkylamidobetaines, alkyl betaines and amphoglycinates, alkyl phosphates, alkylpolyoxyethylene phoaphates or the corresponding acids, silicone derivatives, e.g. alkyl dimethiconecoplyol.

Suitable consistency factors are e.g. fatty alcohols or their mixtures with fatty acid esters, e.g. acetylated lanolin alcohol, aluminum stearates, carbomer, cetyl alcohol, glyceryl oleate, glyceryl stearate, glyceryl stearate (and) PEG 100 stearate, magnesium stearate, magnesium sulfate, oleic acid, stearic acid, stearyl alcohol, myristyl myristate, isopropyl palmitate, beeswax and synthetic equivalents thereof, carbomers, and the like. Suitable conditioners are e.g. alkylamido ammonium lactate, cetrimonium chloride and distearoylethyl hydroxyethylmonium methosulfate and cetearyl alcohol, cetyl dimethicone, cetyl ricinoleate, dimethicone, laureth-23, laureth-4, polydecene, retinyl palmitate, quaternized protein hydrolysates, quaternized cellulose and starch derivatives, quaternized copolymers of acrylic or methacrylic acid or salts, quaternized silicone derivatives.

Suitable emollients are e.g. cetearyl isononanoate, cetearyl octanoate, decyl oleate, isooctyl stearate, coco caprylate/caprate, ethylhexyl hydroxystearate, ethylhexyl isononanoate, isopropyl isostearate, isopropyl myristate, oleyl oleate, hexyl laurate, paraffinum liquidum, PEG-75 lanolin, PEG-7 glyceryl cocoate, petrolatum, ozokerite cyclomethicone, dimethicone, dimethicone copolyol, dicaprylyl ether, butyrospermum parkii, buxus chinensis, canola, carnauba cera, copernicia cerifera, oenothera biennis, elaeis guineensis, prunus dulcis, squalane, zea mays, glycine soja, helianthus annuus, lanolin, hydrogenated castor oil, hydrogenated coconut oil, hydrogenated polyisobutene, sucrose cocoate, stearoxy dimethicone, lanolin alcohol, isohexadecane.

Suitable skin care ingredients are e.g. plant extracts, bisabolol, anti-inflammatory agents, urea, allantoin, panthenol and panthenol derivatives, phytantriol, vitamins A, E, C, D, ceramides of animal or plant origin, lecithins, and the like.

Suitable moisturizers are e.g. butylenes glycol, cetyl alcohol, dimethicone, dimyristyl tartrate, glucose glycereth-26, glycerin, glyceryl stearate, hydrolyzed milk protein, lactic acid, lactose and other sugars, laureth-8, lecithin, octoxyglycerin, PEG-12, PEG 135, PEG-150, PEG-20, PEG-8, pentylene glycol, hexylene glycol, phytantriol, poly quaternium-39 PPG-20 methyl glucose ether, propylene glycol, sodium hyaluronate, sodium lactate, sodium PCA, sorbitol, succinoglycan, synthetic beeswax, tri-C14-15 alkyl citrate, starch.

Suitable thickeners are e.g. acrylates/steareth-20 methacrylate copolymer, carbomer, carboxymethyl starch, cera alba, dimethicone/vinyl dimethicone crosspolymer, propylene glycol alginate, hydroxyethylcellulose, hydroxypropyl methylcellulose, silica, silica dimethyl silylate, xanthan gum, hydrogenated butylenes/ethylene/styrene copolymer.

Suitable lubricants are e.g. adipic acid, fumaric acid and its salts, benzoic acid and its salts, glycerine triacetate, sodium or magnesium lauryl sulfate, magnesium stearate, solid polyethylenglycol, polyvinylpyrrolidone, boric acid, mono-laurate or mono-palmitate, myristyl alcohol, cetyl alcohol, cetylstearyl alcohol, talcum, calcium or magnesium salts of higher fatty acids, mono-, di- or triglycerides of higher fatty acids, polytetrafluorethylen.

Suitable antioxidants are e.g. sulfites, e.g. sodium sulfite, tocopherol or derivates thereof, ascorbic acid or derivates thereof, citric acid, propyl gallate, chitosan glycolate, cysteine, N-acetyl cysteine plus zinc sulfate, thiosulfates, e.g. sodium thiosulfate, polyphenoles and the like.

The compositions may further contain active ingredients, e.g. anti-microbials, anti-inflammatories, plant extracts, bisabolol, panthenol, tocopherol, actives for anti-stinging, anti-irritant or anti-dandruff applications, or anti-aging agents such as retinol, meliobiose and the like. Other suitable actives are e.g. Medicago officinalis, Actinidia chinensis, allantoin, Aloe barbadensis, Anona cherimolia, Anthemis nobilis, Arachis hypogaea, Arnica Montana, Avena sativa, beta-carotene, bisabolol, Borago officinalis, butylenes glycol, Calendula officinalis, Camellia sinensis, camphor, Candida bombicola, capryloyl glycine, Carica papaya, Centaurea cyanus, cetylpyridinium chloride, Chamomilla recutita, Chenopodium quinoa, Chinchona succirubra, Chondrus crispus, Citrus aurantium dulcis, Citrus grandis, Citrus limonum, Cocos nucifera, Coffea Arabica, Crataegus monogina, Cucumis melo, dichlorophenyl imidazoldioxolan, Enteromorpha compressa, Equisetum arvense, ethoxydiglycol, ethyl panthenol, farnesol, ferulic acid, Fragaria chiloensis, Gentiana lutea, Ginkgo biloba, glycerin, glyceryl laurate, Glycyrrhiza glabra, Hamamelis virginiana, heliotropine, hydrogenated palm glycerides, citrates, hydrolyzed castor oil, hydrolyzed wheat protein, Hypericum perforatum, Iris florentina, Juniperus communis, Lactis proteinum, lactose, Lawsonia inermis, linalool, Linum usitatissimum, lysine, magnesium aspartate, Magnifera indica, Malva sylvestris, mannitol, mel Melaleuca alternifolia, Mentha piperita, menthol, menthyl lactate, Mimosa tenuiflora, Nymphaea alba, olaflur, Oryza sativa, panthenol, paraffinum liquidum, PEG-20M, PEG-26 jojoba acid, PEG-26 jojoba alcohol, PEG-35 castor oil, PEG-40 hydrogenated castor oil, PEG-60 hydrogenated castor oil, PEG-8 caprylic/capric acid, Persea gratissima, petrolatum, potassium aspartate, potassium sorbate, propylene glycol, Prunus amygdalus dulcis, Prunus armeniaca, Prunus persica, retinyl palmitate, Ricinus communis, Rosa canina, Rosmarinus officinal's, Rubus idaeus, salicylic acid, Sambucus nigra, sarcosine. Serenoa serrulata, Simmondsia chinensis, sodium carboxymethyl betaglucan, sodium cocoyl amino acids, sodium hyaluronate, sodium palmitoyl praline, stearoxytrimethylsilane, stearyl alcohol, sulfurized TEA-ricinoleate, talc, Thymus vulgaris, Tilia cordata, tocopherol, tocopheryl acetate, trideceth-9, triticum vulgare, tyrosine, undecylenoyl glycine, urea, Vaccinium myrtillus, valine, zinc oxide, zinc sulfate.

The multifunctional composition of the present disclosure can be used in emulsions (both oil-in-water and water-in-oil), in aqueous solutions, in PIT (phase inversion temperature) emulsions, in oily solutions, in foaming cosmetic formulations (foams), and in so-called multiple emulsions, e.g. in triple emulsions (such as water/oil/water emulsions).

The multifunctional composition of the present disclosure can also be formulated as creams, gels, liquids or lotions. They can be used in shampoos, hair conditioners, hair dyes, hair preparations, aftershave lotions, bath soaps and detergents, fragrance preparations, sun care products, indoor tanning products, body and hand preparations, personal cleansers, shaving preparations, tonics, dressings and other hair grooming aids, moisturizing preparations, skin care preparations, wipes and the like. These compositions can be also used in a variety of non-personal care products.

The present disclosure may be better understood with reference to the following examples.

Example No. 1

The following compositions were formulated and tested for antimicrobial efficacy. In particular, the compositions were tested for minimum inhibitory concentration (MIC).

TABLE 1

| Sample No. | 1 | 2 | 3 | 4 | 5 | 6 | 7 |
|---|---|---|---|---|---|---|---|
| 1,3 Propanediol | 50% | 50% | 50% | 50% | 37.50% | 26% | 77.50% |
| Water | | | | | | | |
| Glyceryl Caprylate | 27.50% | | | | | | |
| Polyglyceryl-10 Decaoleate | | 27.50% | | | | | |
| Polyglyceryl-10 Caprylate/Caprate | | | 27.50% | | | | |
| Polyglyceryl-10 Oleate | | | | 27.50% | 40% | 40% | |
| Vanillin | 20% | 20% | 20% | 20% | 20% | 30% | 20% |
| Octanoic Acid (Caprylic Acid) | 2.50% | 2.50% | 2.50% | 2.50% | 2.50% | 4.00% | 2.50% |

The above compositions were screened for their compatibility and for their efficacy against bacteria and fungi. Sample Nos. 3 and 4 above were the most stable. Sample No. 7 was formulated to determine if vanillin was soluble in 1,3 propanediol. The blend was homogeneous, but needed longer mixing times than Sample Nos. 3 and 4.

Sample No. 4 above was then used as a basis for further testing. In particular, Sample No. 4 was tested and compared against other blends and against individual ingredients. The stock solutions for the following tests were made up in alcohol.

Staphylococcus aureus ATCC 6538, Pseudomonas aeruginosa ATCC 9027, Klebsiella pneumonia ATCC 4352, Burkholderia cepacia ATCC 25416, Enterobacter gergoviae ATCC 33028, Candida albicans ATCC 10231, Aspergillus brasiliensis ATCC 16404, and 2 Penicillium sp. were revived from refrigerated slants and plated on TSA plates for bacteria, SDA plates for yeast, and PDA plates for mold. The broth media used for MIC determination on microtiter plates were TSB for bacteria and SDB for fungi.

All prepared solutions were considered as products and were tested at the concentration starting at 10,000 ppm per product. Samples were diluted with 2-fold serial dilution into the appropriate broth media on microtiter plates. The bacterial inoculum at concentration of $1\times10^6$ CFUs/mL and fungal inoculum at concentration of $1\times10^5$ cells or spores/mL were suspended in regular strength broth and added to the wells in 1:1 ratio to the sample/medium mixtures on microtiter plates. The final concentration of bacteria was $5\times10^5$ CFUs/mL; the final concentration of fungi was $5\times10^4$ cells or spores/mL. Bacterial plates were incubated at 35° C. for 2 days and fungal plates were incubated at 28° C. for 5 days before reading results.

The following compositions were formulated and provided the following results:

TABLE 2

| Treatment | S. aureus | Ps. aeruginosa | K. pneumonia | E. gergoviae | B. cepacia | C. albicans | A. brasiliensis | Penicillium sp. |
|---|---|---|---|---|---|---|---|---|
| Sample No. 4 | >10,000 | >10,000 | >10,000 | >10,000 | 5,000 | 1,250 | 5,000 | 1,250 |
| 20% Vanillin | 10,000 | 5,000 | 10,000 | 10,000 | 5,000 | 2,500 | 5,000 | 2,500 |
| 27.5% Polyglyceryl 10 Oleate | >10,000 | >10,000 | >10,000 | >10,000 | >10,000 | >10,000 | >10,000 | >10,000 |
| 50% 1,3-Propanediol | >10,000 | 10,000 | >10,000 | >10,000 | 10,000 | 10,000 | >10,000 | >10,000 |
| 2.5% Octanoic Acid | >10,000 | 10,000 | >10,000 | >10,000 | 10,000 | 2,500 | >10,000 | 7,500 |
| 20% Vanillin + 27.5% Polyclyyceryl 10 Oleate | >10,000 | 5,000 | 10,000 | 10,000 | 5,000 | 2,500 | 5,000 | 2,500 |
| 20% Vanillin + 27.5% Polyclyyceryl 10 Oleate + 50% 1,3-Propanediol | 10,000 | 5,000 | 10,000 | 10,000 | 5,000 | 2,500 | 5,000 | 2,500 |
| 27.5% Polyglyceryl 10 Oleate + 50% 1,3-Propanediol | >10,000 | >10,000 | >10,000 | >10,000 | >10,000 | >10,000 | >10,000 | >10,000 |
| 20% Vanillin + 50% 1,3-Propanediol | 7,500 | 5,000 | 7,500 | 7,500 | 5,000 | 2,500 | 5,000 | 2,500 |
| 20% Vanillin + 27.5% Polyglyceryl 10 Oleate + 2.5% Octanoic Acid | >10,000 | >10,000 | >10,000 | >10,000 | 5,000 | 1,250 | 5,000 | 2,500 |
| 20% Vanillin + 2.5% Octanoic Acid | 5,000 | 5,000 | 5,000 | 5,000 | 5,000 | 1,250 | 5,000 | 2,500 |

As shown above, the combination of vanillin and octanoic acid was more efficacious than either component alone.

To further investigate the synergistic effect of blending vanillin with an organic acid, the following series of combinations were put together in a model cosmetic formulation. The target concentration is the first number and the actual concentration achieved is shown in parentheses (Table 3). The vanillin was presolubilized in DMSO before adding to the formulation so a DMSO control was also included. These samples were then subjected to a CTFA challenge and the effects of the different combinations examined for evidence of synergy.

The formulations tested and the test results are as follows:

TABLE 3

| Exp | | % of Mix | | % of Mix | | % of Mix | | % of Mix | pH |
|---|---|---|---|---|---|---|---|---|---|
| 1 | Octanoic Acid | 250 ppm (251 ppm) | | | | | | | 6.75 |
| 2 | Zemea (1,3-Propanediol) | 5000 ppm (5058 ppm) | | | | | | | 6.6 |
| 3 | Polyglyceryl 10 Oleate | 2750 ppm (2772 ppm) | | | | | | | 6.45 |
| 4 (1% DMSO) | Vanillin | 2000 ppm (2010 ppm) | | | | | | | 6.65 |
| 5 | Octanoic Acid | 250 ppm (245 ppm) | Zemea (1,3-Propanediol) | 5000 ppm (5421 ppm) | | | | | 6.35 |
| 6 | Octanoic Acid | 250 ppm (248 ppm) | Polyglyceryl 10 Oleate | 2750 ppm (2747 ppm) | | | | | 6.51 |
| 7 (1% DMSO) | Octanoic Acid | 250 ppm (248 ppm) | Vanillin | 2000 ppm (2028 ppm) | | | | | 6.9 |
| 8 | Zemea (1,3-Propanediol) | 5000 ppm (5023 ppm) | Polyglyceryl 10 Oleate | 2750 ppm (2808 ppm) | | | | | 6.6 |
| 9 (1% DMSO) | Zemea (1,3-Propanediol) | 5000 ppm (4938 ppm) | Vanillin | 2000 ppm (1998 ppm) | | | | | 6.96 |
| 10 (1% DMSO) | Polyglyceryl 10 Oleate | 2750 ppm (2826 ppm) | Vanillin | 2000 ppm (2008 ppm) | | | | | 6.55 |
| 11 | Octanoic Acid | 250 ppm (242 ppm) | Zemea | 5000 ppm (5047 ppm) | Polyglyceryl 10 Oleate | 2750 ppm (2774 ppm) | | | 6.8 |
| 12 (1% DMSO) | Octanoic Acid | 250 ppm (250 ppm) | Zemea | 5000 ppm (5015 ppm) | Vanillin | 2000 ppm (2020 ppm) | | | 6.3 |

TABLE 3-continued

| Exp | | % of Mix | | % of Mix | | % of Mix | | % of Mix | | pH |
|---|---|---|---|---|---|---|---|---|---|---|
| 13 (1% DMSO) | Octanoic Acid | 250 ppm (253 ppm) | Polyglyceryl 10 Oleate | 2750 ppm (2890 ppm) | Vanillin | 2000 ppm (1999 ppm) | | | | 6.35 |
| 14 (1% DMSO) | Zemea | 5000 ppm (4986 ppm) | Polyglyceryl 10 Oleate | 2750 ppm (2784 ppm) | Vanillin | 2000 ppm (2007 ppm) | | | | 6.5 |
| 15 (1% DMSO) | Octanoic Acid | 250 ppm (287 ppm) | Zemea | 5000 ppm (5021 ppm) | Polyglyceryl 10 Oleate | 2750 ppm (2799 ppm) | Vanillin | 2000 ppm (2009 ppm) | | 6.85 |
| C1 | Unpreserved control | | | | | | | | | 6.8 |
| C2 | DMSO control | 1.0% DMSO | | | | | | | | 6.2 |

TABLE 4

Time zero CTFA challenge data

| Exp | S. aureus | Kp/Eg | Pa/Bc | Candida | Molds |
|---|---|---|---|---|---|
| 1 | $10^6$ | $10^6$ | $10^5$ | $10^5$ | |
| 2 | $10^6$ | $10^6$ | $10^6$ | $10^5$ | $10^5$ |
| 3 | $10^6$ | $10^6$ | $10^6$ | $10^5$ | $10^5$ |
| 4 | $10^6$ | $10^6$ | $10^6$ | $10^5$ | $10^5$ |
| 5 | $10^6$ | $10^6$ | $10^6$ | $10^5$ | $10^5$ |
| 6 | $10^6$ | $10^6$ | $10^6$ | $10^5$ | $10^5$ |
| 7 | $10^6$ | $10^6$ | $10^6$ | $10^5$ | $10^5$ |
| 8 | $10^6$ | $10^6$ | $10^6$ | $10^5$ | $10^5$ |
| 9 | $10^6$ | $10^6$ | $10^6$ | $10^5$ | $10^5$ |
| 10 | $10^6$ | $10^6$ | $10^6$ | $10^5$ | $10^5$ |
| 11 | $10^6$ | $10^6$ | $10^6$ | $10^5$ | $10^5$ |
| 12 | $10^6$ | $10^6$ | $10^6$ | $10^5$ | $10^5$ |
| 13 | $10^6$ | $10^6$ | $10^6$ | $10^5$ | $10^5$ |
| 14 | $10^6$ | $10^6$ | $10^6$ | $10^5$ | $10^5$ |
| 15 | $10^6$ | $10^6$ | $10^6$ | $10^5$ | $10^5$ |
| C1 | $10^6$ | $10^6$ | $10^6$ | $10^5$ | $10^5$ |
| C2 | $10^6$ | $10^6$ | $10^6$ | $10^5$ | $10^5$ |

TABLE 5

T = 24 hours CTFA challenge data

| Exp | S. aureus | Kp/Eg | Pa/Bc | Candida | Molds |
|---|---|---|---|---|---|
| 1 | $10^6$ | $10^5$ | $10^6$ | $10^4$ | $10^5$ |
| 2 | $10^6$ | $10^6$ | $10^6$ | $10^4$ | $10^5$ |
| 3 | $10^6$ | $10^6$ | $10^6$ | $10^5$ | $10^5$ |
| 4 | $3 \times 10^2$ | 20 | 90 | $1 \times 10^3$ | $10^5$ |
| 5 | $6 \times 10^4$ | $1 \times 10^4$ | $10^6$ | $10^5$ | $10^5$ |
| 6 | $10^6$ | $10^6$ | $10^6$ | $10^5$ | $10^5$ |
| 7 | <10 | <10 | <10 | $10^4$ | $10^3$ |
| 8 | $10^6$ | $10^6$ | $10^6$ | $10^5$ | $10^5$ |
| 9 | <10 | <10 | <10 | <10 | 90 |
| 10 | $1.2 \times 10^2$ | $9 \times 10^2$ | $2 \times 10^3$ | $4 \times 10^2$ | $10^4$ |
| 11 | $10^6$ | $10^5$ | $10^5$ | $10^4$ | $10^5$ |
| 12 | <10 | <10 | <10 | <10 | 60 |
| 13 | 40 | 20 | <10 | 10 | 400 |
| 14 | <10 | <10 | <10 | <10 | 40 |
| 15 | <10 | <10 | <10 | <10 | 30 |
| C1 | $10^6$ | $10^6$ | $10^6$ | $10^5$ | $10^5$ |
| C2 | $10^6$ | $10^6$ | $10^6$ | $10^5$ | $10^5$ |

TABLE 6

T = 48 hours CTFA challenge data

| Exp | S. aureus | Kp/Eg | Pa/Bc | Candida | Molds |
|---|---|---|---|---|---|
| 1 | $10^5$ | $10^5$ | $10^6$ | $10^4$ | $10^5$ |
| 2 | $10^6$ | $10^6$ | $10^6$ | $10^3$ | $10^5$ |
| 3 | $10^6$ | $10^6$ | $10^6$ | $10^4$ | $10^5$ |
| 4 | 50 | <10 | 20 | 400 | $10^4$ |
| 5 | $4 \times 10^3$ | $9 \times 10^3$ | $1.2 \times 10^4$ | $10^4$ | $10^5$ |
| 6 | $10^6$ | $10^5$ | $10^6$ | $10^4$ | $10^5$ |

TABLE 6-continued

T = 48 hours CTFA challenge data

| Exp | S. aureus | Kp/Eg | Pa/Bc | Candida | Molds |
|---|---|---|---|---|---|
| 7 | <10 | <10 | <10 | $5 \times 10^3$ | $7 \times 10^2$ |
| 8 | $10^6$ | $10^6$ | $10^6$ | $10^4$ | $10^5$ |
| 9 | <10 | <10 | <10 | <10 | 40 |
| 10 | 40 | $2 \times 10^2$ | $4 \times 10^2$ | 120 | $4 \times 10^3$ |
| 11 | $10^5$ | $10^4$ | $10^5$ | $7.1 \times 10^3$ | $10^5$ |
| 12 | <10 | <10 | <10 | <10 | 10 |
| 13 | 10 | <10 | <10 | <10 | 240 |
| 14 | <10 | <10 | <10 | <10 | 10 |
| 15 | <10 | <10 | <10 | <10 | 10 |
| C1 | $10^6$ | $10^6$ | $10^6$ | $10^5$ | $10^5$ |
| C2 | $10^6$ | $10^6$ | $10^6$ | $10^5$ | $10^5$ |

TABLE 7

T = 1 week CTFA challenge data

| Exp | S. aureus | Kp/Eg | Pa/Bc | Candida | Molds |
|---|---|---|---|---|---|
| 1 | $10^5$ | $10^6$ | $10^5$ | $9 \times 10^2$ | $10^4$ |
| 2 | $10^6$ | $10^5$ | $10^6$ | $10^3$ | $10^4$ |
| 3 | $10^6$ | $10^6$ | $10^6$ | $10^4$ | $10^3$ |
| 4 | <10 | <10 | <10 | <10 | <10 |
| 5 | <10 | 60 | 90 | $5 \times 10^3$ | $10^4$ |
| 6 | $10^6$ | $10^5$ | $10^6$ | $10^4$ | $10^4$ |
| 7 | <10 | <10 | <10 | <10 | <10 |
| 8 | $10^6$ | $10^6$ | $10^6$ | $9 \times 10^3$ | $10^4$ |
| 9 | <10 | <10 | <10 | <10 | <10 |
| 10 | <10 | 10 | <10 | <10 | <10 |
| 11 | $3 \times 10^2$ | $1.6 \times 10^2$ | $6 \times 10^2$ | <10 | $10^4$ |
| 12 | <10 | <10 | <10 | <10 | <10 |
| 13 | 10 | <10 | <10 | <10 | <10 |
| 14 | <10 | <10 | <10 | <10 | <10 |
| 15 | <10 | <10 | <10 | <10 | <10 |
| C1 | $10^6$ | $10^6$ | $10^6$ | $10^5$ | $10^5$ |
| C2 | $10^6$ | $10^6$ | $10^6$ | $10^5$ | $10^5$ |

An examination of the data generated in the test reveals that the blend of vanillin and an organic acid has synergistic activity.

Having demonstrated good efficacy in one formulation, CTFA challenge testing was carried out to show that the composition of the present disclosure may be broadly used to protect all types of personal care formulations from microbial contamination.

Samples Tested
Makeup Remover
Unpreserved Control
Preserved with 1.0% Sample No. 4
Preserved with 2.0% Sample No. 4
Conditioner
Unpreserved Control
Preserved with 1.0% Sample No. 4
Preserved with 2.0% Sample No. 4

Mascara
Unpreserved Control
Preserved with 1.0% Sample No. 4
Water in Oil Lotion
Unpreserved Control
Preserved with 1.0% Sample No. 4
Oil in Water Lotion 1
Unpreserved Control
Preserved with 1.0% Sample No. 4
Oil in Water Lotion 2
Unpreserved Control
Preserved with 2.0% Sample No. 4

The CTFA cosmetic challenge protocol was followed using five separate inocula:

Pool 1 *Staphylococcus aureus* (ATCC 6538),
Pool 2 *Pseudomonas aeruginosa* (ATCC 9027)+*Burkholderia cepacia* (ATCC 25416),
Pool 3 *Klebsiella pneumoniae* (ATCC 4352)+*Enterobacter gergoviae* (ATCC 33028),
Pool 4 *Candida albicans* (ATCC 10231),
Pool 5 *Aspergillus brasiliensis* (ATCC 16404)+2 *Penicillium* sp. isolated from cosmetic products Samples (35 grams each) were inoculated with approximately 2,000,000 bacteria per gram or 100,000 yeast cells or mold spores per gram. Individual challenges were prepared from overnight slants of bacteria and yeast cultures and from heavily sporulating mold cultures, 7 to 10 days old. All samples were plated (Bacteria in Tryptic Soy agar and Fungi in Malt Agar) quantitatively for viable organisms after 24 hours and weekly for 4 weeks. Modified Letheen Broth with 0.5% Tween 80 and 0.07% Lecithin added was used as a neutralizer. Samples inoculated with mold spores were also plated after 48 hours. Four weeks after the initial challenge, samples were challenged again and the same sampling regime followed.

The composition was added to these formulations to give a final concentration of 1-2% and tested to see if able to provide significant protection as determined by the industry standard challenge test.

The challenge test data for all the formulations tested are shown below Results are expressed as colony forming units per gram (CFU/g).

TABLE 8

Inoculum - Colony Forming Units Added per Gram (CFU/g) of Product

| Organism | Challenge #1 | Challenge #2 |
|---|---|---|
| S. aureus | $2.0 \times 10^6$ | $2.9 \times 10^6$ |
| P. aeruginosa + B. cepacia | $4.5 \times 10^6$ | $4.0 \times 10^6$ |
| K. pneumoniae + E. gergoviae | $2.3 \times 10^6$ | $1.7 \times 10^6$ |
| C. albicans | $1.2 \times 10^5$ | $8.4 \times 10^4$ |
| Mixed Molds | $1.4 \times 10^5$ | $1.3 \times 10^5$ |

TABLE 9

Makeup Remover Unfragranced Control - Colony Forming Units per Gram (CFU/g)

| Test Organism | 0 Hours | 24 Hours | 48 Hours | 7 Days | 14 Days | 21 Days | 28 Days |
|---|---|---|---|---|---|---|---|
| | | | Challenge # 1 | | | | |
| S. aureus | $6.0 \times 10^3$ | $1.0 \times 10^2$ | — | <10 | <10 | <10 | <10 |
| P. aeruginosa + B. cepacia | $4.9 \times 10^4$ | $<10^2$ | — | <10 | <10 | <10 | <10 |
| K. pneumonia + E. gergoviae | $2.5 \times 10^5$ | $1.0 \times 10^5$ | — | <10 | <10 | <10 | <10 |
| C. albicans | $2.3 \times 10^4$ | $1.1 \times 10^4$ | — | $1.2 \times 10^2$ | <10 | <10 | <10 |
| Mixed Molds | $5.0 \times 10^4$ | $5.0 \times 10^4$ | $5.0 \times 10^4$ | $1.7 \times 10^4$ | $2.5 \times 10^4$ | $8.0 \times 10^4$ | $5.0 \times 10^4$ |
| | | | Challenge # 2 | | | | |
| S. aureus | $2.1 \times 10^4$ | <10 | — | <10 | <10 | <10 | <10 |
| P. aeruginosa + B. cepacia | $2.0 \times 10^5$ | $>3.0 \times 10^3$ | — | $>3.0 \times 10^3$ | $>3.0 \times 10^5$ | $>3.0 \times 10^5$ | $>3.0 \times 10^5$ |
| K. pneumonia + E. gergoviae | $5.8 \times 10^5$ | $>3.0 \times 10^5$ | — | $>3.0 \times 10^4$ | $>3.0 \times 10^5$ | $>3.0 \times 10^5$ | $>3.0 \times 10^5$ |
| C. albicans | $3.0 \times 10^4$ | $2.2 \times 10^4$ | — | $2.0 \times 10^3$ | <10 | <10 | <10 |
| Mixed Molds | $1.1 \times 10^5$ | $6.0 \times 10^4$ | $1.4 \times 10^5$ | $8.0 \times 10^4$ | $2.8 \times 10^4$ | $8.0 \times 10^4$ | $1.0 \times 10^5$ |

TABLE 10

Makeup Remover with 1.0% Sample No. 4 - Colony Forming Units per Gram (CFU/g)

| | Challenge # 1 | | | | | | Challenge # 2 | | | | | |
|---|---|---|---|---|---|---|---|---|---|---|---|---|
| Test Organism | 24 Hours | 48 Hours | 7 Days | 14 Days | 21 Days | 28 Days | 24 Hours | 48 Hours | 7 Days | 14 Days | 21 Days | 28 Days |
| S. aureus | <10 | — | <10 | <10 | <10 | <10 | <10 | — | <10 | <10 | <10 | <10 |
| P. aeruginoso + B. cepocia | <10 | — | <10 | <10 | <10 | <10 | <10 | — | <10 | <10 | <10 | <10 |
| K. pneumoniae + E. gergoviae | $4.5 \times 10^4$ | — | <10 | <10 | <10 | <10 | $5.5 \times 10^5$ | — | <10 | <10 | <10 | <10 |
| C. albicans | <10 | — | <10 | <10 | <10 | <10 | $1.8 \times 10^2$ | — | <10 | <10 | <10 | <10 |
| Mixed Molds | $6.0 \times 10^3$ | $3.0 \times 10^1$ | <10 | <10 | <10 | <10 | $1.0 \times 10^4$ | $3.4 \times 10^2$ | <10 | <10 | <10 | <10 |

TABLE 11

Makeup Remover with 2.0% Sample No. 4 - Colony Forming Units per Gram (CFU/g)

| | Challenge # 1 | | | | | | Challenge # 2 | | | | | |
|---|---|---|---|---|---|---|---|---|---|---|---|---|
| Test Organism | 24 Hours | 48 Hours | 7 Days | 14 Days | 21 Days | 28 Days | 24 Hours | 48 Hours | 7 Days | 14 Days | 21 Days | 28 Days |
| *S. aureus* | <10 | — | <10 | <10 | <10 | <10 | <10 | — | <10 | <10 | <10 | <10 |
| *P. aeruginoso* + *B. cepocia* | <10 | — | <10 | <10 | <10 | <10 | <10 | — | <10 | <10 | <10 | <10 |
| *K. pneumoniae* + *E. gergoviae* | $6.3 \times 10^4$ | — | <10 | <10 | <10 | <10 | $8.4 \times 10^4$ | — | <10 | <10 | <10 | <10 |
| *C. albicans* | <10 | — | <10 | <10 | <10 | <10 | <10 | — | <10 | <10 | <10 | <10 |
| Mixed Molds | $5.0 \times 10^1$ | $2.0 \times 10^1$ | <10 | <10 | <10 | <10 | $5.0 \times 10^1$ | $2.0 \times 10^1$ | <10 | <10 | <10 | <10 |

TABLE 12

Hair Conditioner Unfragranced Control - Colony Forming Units per Gram (CFU/g)

| Test Organism | 0 Hours | 24 Hours | 48 Hours | 7 Days | 14 Days | 21 Days | 28 Days |
|---|---|---|---|---|---|---|---|
| Challenge # 1 | | | | | | | |
| *S. aureus* | $8.2 \times 10^5$ | $3.5 \times 10^5$ | — | $1.4 \times 10^4$ | $2.3 \times 10^3$ | <10 | <10 |
| *P. aeruginosa* + *B. cepacia* | $1.4 \times 10^6$ | $9.0 \times 10^6$ | — | $>3.0 \times 10^7$ | $>3.0 \times 10^7$ | $>3.0 \times 10^7$ | $>3.0 \times 10^7$ |
| *K. pneumonia* + *E. gergoviae* | $9.3 \times 10^5$ | $1.8 \times 10^7$ | — | $>3.0 \times 10^7$ | $>3.0 \times 10^7$ | $>3.0 \times 10^7$ | $>3.0 \times 10^7$ |
| *C. albicans* | $6.5 \times 10^4$ | $1.3 \times 10^5$ | — | $2.6 \times 10^6$ | $2.4 \times 10^6$ | $1.3 \times 10^7$ | $>10^7$ |
| Mixed Molds | $6.0 \times 10^4$ | $7.0 \times 10^4$ | $7.0 \times 10^4$ | $<10^2$ | $<10^2$ | <10 | $2.0 \times 10^2$ |
| Challenge # 2 | | | | | | | |
| *S. aureus* | $1.1 \times 10^6$ | $2.3 \times 10^5$ | — | $1.0 \times 10^2$ | <10 | <10 | <10 |
| *P. aeruginosa* + *B. cepacia* | $>3.0 \times 10^7$ | $>3.0 \times 10^7$ | — | $>3.0 \times 10^7$ | $>3.0 \times 10^7$ | $>3.0 \times 10^7$ | $>3.0 \times 10^7$ |
| *K. pneumonia* + *E. gergoviae* | $>3.0 \times 10^7$ | $>3.0 \times 10^7$ | — | $>3.0 \times 10^7$ | $>3.0 \times 10^7$ | $>3.0 \times 10^7$ | $>3.0 \times 10^7$ |
| *C. albicans* | $>10^7$ | $>10^7$ | — | $>10^7$ | * | * | * |
| Mixed Molds | $7.0 \times 10^4$ | $1.4 \times 10^5$ | $9.0 \times 10^4$ | <10 | <10 | <10 | <10 |

*Bacterial Contamination

TABLE 13

Hair Conditioner with 1.0% Sample No. 4 - Colony Forming Units per Gram (CFU/g)

| Test Organism | 24 Hours | 48 Hours | 7 Days | 14 Days | 21 Days | 28 Days |
|---|---|---|---|---|---|---|
| Challenge # 1 | | | | | | |
| *S. aureus* | $2.1 \times 10^2$ | — | <10 | <10 | <10 | <10 |
| *P. aeruginoso* + *B. cepocia* | $3.3 \times 10^5$ | — | $1.2 \times 10^6$ | $1.1 \times 10^5$ | $1.1 \times 10^5$ | $>3.0 \times 10^6$ |
| *K. pneumoniae* + *E. gergoviae* | $2.4 \times 10^5$ | — | $1.9 \times 10^5$ | $3.5 \times 10^5$ | $3.5 \times 10^5$ | $>3.0 \times 10^6$ |
| *C. albicans* | $4.5 \times 10^4$ | — | <10 | <10 | <10 | <10 |
| Mixed Molds | $7.0 \times 10^3$ | $5.0 \times 10^1$ | $2.0 \times 10^1$ | <10 | <10 | <10 |
| Challenge # 2 | | | | | | |
| *S. aureus* | <10 | — | <10 | <10 | <10 | <10 |
| *P. aeruginoso* + *B. cepocia* | $>3.0 \times 10^6$ | — | $>3.0 \times 10^6$ | $>3.0 \times 10^6$ | $>3.0 \times 10^6$ | $>3.0 \times 10^6$ |
| *K. pneumoniae* + *E. gergoviae* | $>3.0 \times 10^6$ | — | $>3.0 \times 10^6$ | $>3.0 \times 10^6$ | $>3.0 \times 10^6$ | $>3.0 \times 10^6$ |
| *C. albicans* | $4.0 \times 10^4$ | — | <10 | <10 | <10 | <10 |
| Mixed Molds | $9.0 \times 10^3$ | $1.0 \times 10^2$ | <10 | <10 | <10 | <10 |

TABLE 14

Hair Conditioner with 2.0% Sample No. 4 - Colony Forming Units per Gram (CFU/g)

| | Challenge # 1 | | | | | | Challenge # 2 | | | | | |
|---|---|---|---|---|---|---|---|---|---|---|---|---|
| Test Organism | 24 Hours | 48 Hours | 7 Days | 14 Days | 21 Days | 28 Days | 24 Hours | 48 Hours | 7 Days | 14 Days | 21 Days | 28 Days |
| S. aureus | <10 | — | <10 | <10 | <10 | <10 | <10 | — | <10 | <10 | <10 | <10 |
| P. aeruginoso + B. cepocia | $8.6 \times 10^3$ | — | <10 | <10 | <10 | <10 | $>3.0 \times 10^5$ | — | <10 | <10 | <10 | <10 |
| K. pneumoniae + E. gergoviae | $1.1 \times 10^5$ | — | <10 | <10 | <10 | <10 | $2.6 \times 10^5$ | — | <10 | <10 | <10 | <10 |
| C. albicans | <10 | — | <10 | <10 | <10 | <10 | $3.7 \times 10^2$ | — | <10 | <10 | <10 | <10 |
| Mixed Molds | $6.0 \times 10^2$ | <10 | <10 | <10 | <10 | <10 | $5.0 \times 10^3$ | <10 | <10 | <10 | <10 | <10 |

TABLE 15

Mascara Unfragranced Control - Colony Forming Units per Gram (CFU/g)

| Test Organism | 0 Hours | 24 Hours | 48 Hours | 7 Days | 14 Days | 21 Days | 28 Days |
|---|---|---|---|---|---|---|---|
| Challenge # 1 | | | | | | | |
| S. aureus | $6.7 \times 10^5$ | $5.1 \times 10^5$ | — | $5.9 \times 10^4$ | <10 | <10 | <10 |
| P. aeruginosa + B. cepacia | $7.1 \times 10^5$ | $1.0 \times 10^5$ | — | <10 | <10 | <10 | <10 |
| K. pneumonia + E. gergoviae | $4.4 \times 10^5$ | $1.1 \times 10^5$ | — | $3.5 \times 10^2$ | <10 | <10 | <10 |
| C. albicans | $4.5 \times 10^4$ | $9.6 \times 10^3$ | — | $2.6 \times 10^2$ | <10 | <10 | <10 |
| Mixed Molds | $3.0 \times 10^4$ | $6.0 \times 10^4$ | $4.0 \times 10^4$ | $1.8 \times 10^4$ | $1.4 \times 10^4$ | $5.0 \times 10^3$ | $5.0 \times 10^3$ |
| Challenge # 2 | | | | | | | |
| S. aureus | $1.3 \times 10^6$ | $1.5 \times 10^6$ | — | $1.5 \times 10^5$ | $1.7 \times 10^2$ | <10 | <10 |
| P. aeruginosa + B. cepacia | $1.5 \times 10^6$ | $2.5 \times 10^4$ | — | <10 | <10 | <10 | <10 |
| K. pneumonia + E. gergoviae | $2.1 \times 10^6$ | $1.8 \times 10^5$ | — | $1.0 \times 10^1$ | <10 | <10 | <10 |
| C. albicans | $5.2 \times 10^4$ | $1.9 \times 10^4$ | — | $<10^3$ | $2.1 \times 10^2$ | <10 | <10 |
| Mixed Molds | $1.1 \times 10^5$ | $2.2 \times 10^5$ | $7.0 \times 10^4$ | $1.2 \times 10^5$ | $6.0 \times 10^4$ | $3.7 \times 10^4$ | $5.0 \times 10^4$ |

TABLE 16

Mascara with 1.0% Sample No. 4 - Colony Forming Units per Gram (CFU/g)

| Test Organism | 24 Hours | 48 Hours | 7 Days | 14 Days | 21 Days | 28 Days |
|---|---|---|---|---|---|---|
| Challenge # 1 | | | | | | |
| S. aureus | $8.3 \times 10^4$ | — | $1.0 \times 10^1$ | <10 | <10 | <10 |
| P. aeruginoso + B. cepocia | $2.2 \times 10^4$ | — | <10 | <10 | <10 | <10 |
| K. pneumoniae + E. gergoviae | $1.1 \times 10^5$ | — | <10 | <10 | <10 | <10 |
| C. albicans | <10 | — | <10 | <10 | <10 | <10 |
| Mixed Molds | $1.0 \times 10^3$ | $1.6 \times 10^3$ | $2.0 \times 10^1$ | <10 | <10 | <10 |
| Challenge # 2 | | | | | | |
| S. aureus | $2.2 \times 10^5$ | — | <10 | <10 | <10 | <10 |
| P. aeruginosa + B. cepocia | $2.5 \times 10^4$ | — | <10 | <10 | <10 | <10 |
| K. pneumoniae + E. gergoviae | $1.8 \times 10^5$ | — | <10 | <10 | <10 | <10 |
| C. albicans | $1.9 \times 10^4$ | — | <10 | <10 | <10 | <10 |
| Mixed Molds | $2.2 \times 10^5$ | $2.0 \times 10^2$ | $1.0 \times 10^1$ | <10 | <10 | <10 |

TABLE 17

Water in Oil Lotion Unfragranced Control - Colony Forming Units per Gram (CFU/g)

| Test Organism | 0 Hours | 24 Hours | 48 Hours | 7 Days | 14 Days | 21 Days | 28 Days |
|---|---|---|---|---|---|---|---|
| Challenge # 1 | | | | | | | |
| S. aureus | $1.2 \times 10^5$ | $8.2 \times 10^4$ | — | $5.6 \times 10^3$ | * | * | <10 |
| P. aeruginosa + B. cepacia | $5.0 \times 10^4$ | $4.8 \times 10^4$ | — | $1.4 \times 10^5$ | $5.9 \times 10^5$ | $4.5 \times 10^5$ | $4.2 \times 10^4$ |

TABLE 17-continued

Water in Oil Lotion Unfragranced Control - Colony Forming Units per Gram (CFU/g)

| Test Organism | 0 Hours | 24 Hours | 48 Hours | 7 Days | 14 Days | 21 Days | 28 Days |
|---|---|---|---|---|---|---|---|
| K. pneumonia + E. gergoviae | $9.8 \times 10^4$ | $5.7 \times 10^5$ | — | $1.1 \times 10^5$ | * | * | $1.9 \times 10^4$ |
| C. albicans | $7.2 \times 10^3$ | $5.7 \times 10^3$ | — | $1.6 \times 10^3$ | $3.7 \times 10^{3°}$ | $9.3 \times 10^3$ | $4.8 \times 10^3$ |
| Mixed Molds | $1.4 \times 10^4$ | $1.2 \times 10^4$ | $4.0 \times 10^3$ | $1.1 \times 10^3$ | $8.0 \times 10^3$ | $2.0 \times 10^3$ | $1.0 \times 10^3$ |
| Challenge # 2 | | | | | | | |
| S. aureus | $4.3 \times 10^4$ | $5.6 \times 10^4$ | — | $5.1 \times 10^5$ | $1.2 \times 10^3$ | $1.7 \times 10^2$ | $5.0 \times 10^1$ |
| P. aeruginosa + B. cepacia | $6.9 \times 10^5$ | $8.5 \times 10^5$ | — | $5.6 \times 10^5$ | $1.3 \times 10^6$ | $1.5 \times 10^6$ | $1.3 \times 10^6$ |
| K. pneumonia + E. gergoviae | $8.6 \times 10^4$ | $7.4 \times 10^4$ | — | $2.9 \times 10^5$ | $6.9 \times 10^4$ | $2.0 \times 10^5$ | $2.4 \times 10^5$ |
| C. albicans | $4.4 \times 10^3$ | $2.0 \times 10^3$ | — | $3.4 \times 10^4$ | $4.5 \times 10^4$ | $2.7 \times 10^4$ | $5.1 \times 10^4$ |
| Mixed Molds | $1.2 \times 10^4$ | $2.0 \times 10^3$ | $8.0 \times 10^3$ | $3.0 \times 10^4$ | $1.8 \times 10^4$ | $>10^5$ | $>10^5$ |

TABLE 18

Water in Oil Lotion with 1.0% Sample No. 4 - Colony Forming Units per Gram (CFU/g)

| Test Organism | 24 Hours | 48 Hours | 7 Days | 14 Days | 21 Days | 28 Days |
|---|---|---|---|---|---|---|
| Challenge # 1 | | | | | | |
| S. aureus | $7.6 \times 10^4$ | — | $2.5 \times 10^2$ | <10 | <10 | <10 |
| P. aeruginoso + B. cepocia | $5.3 \times 10^3$ | — | <10 | <10 | <10 | <10 |
| K. pneumoniae + E. gergoviae | $2.6 \times 10^4$ | — | <10 | <10 | <10 | <10 |
| C. albicans | $6.3 \times 10^3$ | — | <10 | <10 | <10 | <10 |
| Mixed Molds | $1.0 \times 10^3$ | $6.0 \times 10^1$ | <10 | <10 | <10 | <10 |
| Challenge # 2 | | | | | | |
| S. aureus | $2.1 \times 10^4$ | — | <10 | <10 | <10 | <10 |
| P. aeruginoso + B. cepacia | $6.0 \times 10^3$ | — | <10 | <10 | <10 | <10 |
| K. pneumoniae + E. gergoviae | $3.5 \times 10^4$ | — | <10 | <10 | <10 | <10 |
| C. albicans | $9.0 \times 10^2$ | — | <10 | <10 | <10 | <10 |
| Mixed Molds | $8.0 \times 10^2$ | $1.5 \times 10^2$ | <10 | <10 | <10 | <10 |

TABLE 19

Oil in Water Lotion Unfragranced Control - Colony Forming Units per Gram (CFU/g)

| Test Organism | 0 Hours | 24 Hours | 48 Hours | 7 Days | 14 Days | 21 Days | 28 Days |
|---|---|---|---|---|---|---|---|
| Challenge # 1 | | | | | | | |
| S. aureus | $7.9 \times 10^5$ | $9.8 \times 10^5$ | — | $2.8 \times 10^4$ | $9.0 \times 10^1$ | <10 | <10 |
| P. aeruginosa + B. cepacia | $1.3 \times 10^6$ | $1.3 \times 10^6$ | — | $>3.0 \times 10^6$ | $>3.0 \times 10^7$ | $>3.0 \times 10^7$ | $>3.0 \times 10^7$ |
| K. pneumonia + E. gergoviae | $1.2 \times 10^6$ | $2.0 \times 10^6$ | — | $>3.0 \times 10^6$ | $4.1 \times 10^6$ | $7.3 \times 10^6$ | $1.4 \times 10^7$ |
| C. albicans | $5.0 \times 10^4$ | $6.9 \times 10^4$ | — | $8.6 \times 10^4$ | $1.0 \times 10^3$ | $1.3 \times 10^5$ | $1.5 \times 10^5$ |
| Mixed Molds | $7.0 \times 10^4$ | $1.0 \times 10^5$ | $1.1 \times 10^5$ | $6.0 \times 10^4$ | $4.0 \times 10^4$ | $4.0 \times 10^4$ | $5.0 \times 10^4$ |
| Challenge # 2 | | | | | | | |
| S. aureus | $1.3 \times 10^6$ | $1.9 \times 10^6$ | — | $3.7 \times 10^5$ | $5.0 \times 10^3$ | $1.1 \times 10^3$ | $4.4 \times 10^2$ |
| P. aeruginosa + B. cepacia | $>3.0 \times 10^7$ | $>3.0 \times 10^7$ | — | $6.4 \times 10^7$ | $>3.0 \times 10^7$ | $>3.0 \times 10^7$ | $>3.0 \times 10^7$ |
| K. pneumonia + E. gergoviae | $1.2 \times 10^7$ | $2.1 \times 10^7$ | — | $3.7 \times 10^7$ | $2.1 \times 10^7$ | $2.1 \times 10^7$ | $1.8 \times 10^7$ |
| C. albicans | $2.9 \times 10^6$ | $2.3 \times 10^5$ | — | $2.6 \times 10^5$ | $3.1 \times 10^5$ | $3.3 \times 10^5$ | $>3.0 \times 10^5$ |
| Mixed Molds | $2.0 \times 10^5$ | $9.0 \times 10^4$ | $1.1 \times 10^5$ | $1.7 \times 10^5$ | $9.0 \times 10^4$ | $9.0 \times 10^4$ | $7.0 \times 10^4$ |

TABLE 20

Oil in Water Lotion with 1.0% Sample No. 4 - Colony Forming Units per Gram (CFU/g)

| Test Organism | 24 Hours | 48 Hours | 7 Days | 14 Days | 21 Days | 28 Days |
|---|---|---|---|---|---|---|
| *Challenge # 1* | | | | | | |
| S. aureus | $5.9 \times 10^4$ | — | <10 | <10 | <10 | <10 |
| P. aeruginoso + B. cepocia | $8.6 \times 10^4$ | — | <10 | <10 | <10 | <10 |
| K. pneumoniae + E. gergoviae | <10 | — | <10 | <10 | <10 | <10 |
| C. albicans | $1.2 \times 10^2$ | — | <10 | <10 | <10 | <10 |
| Mixed Molds | $7.0 \times 10^3$ | $5.0 \times 10^3$ | $2.0 \times 10^3$ | $1.8 \times 10^3$ | $6.0 \times 10^2$ | $1.3 \times 10^2$ |
| *Challenge # 2* | | | | | | |
| S. aureus | $1.1 \times 10^4$ | — | <10 | <10 | <10 | <10 |
| P. aeruginoso + B. cepocia | $4.0 \times 10^4$ | — | <10 | <10 | <10 | <10 |
| K. pneumoniae + E. gergoviae | $1.0 \times 10^1$ | — | <10 | <10 | <10 | <10 |
| C. albicans | $3.2 \times 10^2$ | — | <10 | <10 | <10 | <10 |
| Mixed Molds | $2.5 \times 10^4$ | $1.5 \times 10^4$ | $6.0 \times 10^3$ | $3.0 \times 10^3$ | $8.0 \times 10^2$ | $7.0 \times 10^2$ |

TABLE 21

Oil in Water Lotion 2+ Unfragranced Control - Colony Forming Units per Gram (CFU/g)

| Test Organism | 0 Hours | 24 Hours | 48 Hours | 7 Days | 14 Days | 21 Days | 28 Days |
|---|---|---|---|---|---|---|---|
| *Challenge # 1* | | | | | | | |
| S. aureus | $6.9 \times 10^5$ | $4.3 \times 10^5$ | — | $4.7 \times 10^5$ | $3.9 \times 10^5$ | * | $1.2 \times 10^6$ |
| P. aeruginosa + B. cepacia | $9.0 \times 10^5$ | $4.4 \times 10^5$ | — | $>3.0 \times 10^6$ | $>3.0 \times 10^7$ | $>3.0 \times 10^7$ | $>3.0 \times 10^7$ |
| K. pneumonia + E. gergoviae | $9.4 \times 10^5$ | $7.7 \times 10^5$ | — | $>3.0 \times 10^6$ | $3.1 \times 10^7$ | * | $2.7 \times 10^7$ |
| C. albicans | $6.2 \times 10^4$ | $4.5 \times 10^5$ | — | $>3.0 \times 10^6$ | $3.6 \times 10^6$ | $4.1 \times 10^6$ | $4.7 \times 10^6$ |
| Mixed Molds | $8.0 \times 10^4$ | $3.2 \times 10^4$ | $2.1 \times 10^4$ | $4.0 \times 10^4$ | $4.0 \times 10^3$ | $7.0 \times 10^3$ | $7.0 \times 10^3$ |
| *Challenge # 2* | | | | | | | |
| S. aureus | $1.6 \times 10^6$ | $3.0 \times 10^6$ | — | $1.2 \times 10^5$ | $2.3 \times 10^6$ | $2.1 \times 10^6$ | $1.5 \times 10^6$ |
| P. aeruginosa + B. cepacia | $>3.0 \times 10^7$ | $>3.0 \times 10^7$ | — | $>3.0 \times 10^7$ | $>3.0 \times 10^7$ | $>3.0 \times 10^7$ | $>3.0 \times 10^7$ |
| K. pneumonia + E. gergoviae | $>3.0 \times 10^7$ | $>3.0 \times 10^7$ | — | $2.5 \times 10^7$ | $3.3 \times 10^7$ | $>3.0 \times 10^7$ | $2.7 \times 10^7$ |
| C. albicans | $>3.0 \times 10^6$ | $4.0 \times 10^6$ | — | $2.7 \times 10^6$ | $4.3 \times 10^6$ | $4.6 \times 10^6$ | $3.8 \times 10^6$ |
| Mixed Molds | $4.0 \times 10^4$ | $1.4 \times 10^5$ | $6.0 \times 10^4$ | $6.0 \times 10^4$ | $1.2 \times 10^5$ | $5.0 \times 10^4$ | $1.1 \times 10^5$ |

*Bacterial Contamination

TABLE 22

Oil in Water Lotion 2+ with 2.0% Sample No. 4 - Colony Forming Units per Gram (CFU/g)

| Test Organism | Challenge # 1 | | | | | | Challenge # 2 | | | | | |
|---|---|---|---|---|---|---|---|---|---|---|---|---|
| | 24 Hours | 48 Hours | 7 Days | 14 Days | 21 Days | 28 Days | 24 Hours | 48 Hours | 7 Days | 14 Days | 21 Days | 28 Days |
| S. aureus | $1.6 \times 10^2$ | — | <10 | <10 | <10 | <10 | $6.3 \times 10^2$ | — | <10 | <10 | <10 | <10 |
| P. aeruginoso + B. cepocia | $3.9 \times 10^4$ | — | <10 | <10 | <10 | <10 | $3.1 \times 10^4$ | — | <10 | <10 | <10 | <10 |
| K. pneumoniae + E. gergoviae | $8.6 \times 10^4$ | — | <10 | <10 | <10 | <10 | $1.1 \times 10^5$ | — | <10 | <10 | <10 | <10 |
| C. albicans | $4.5 \times 10^4$ | — | <10 | <10 | <10 | <10 | $7.8 \times 10^4$ | — | <10 | <10 | <10 | <10 |
| Mixed Molds | $1.4 \times 10^3$ | $3.0 \times 10^1$ | <10 | <10 | <10 | <10 | $2.3 \times 10^3$ | $2.0 \times 10^1$ | <10 | <10 | <10 | <10 |

As shown above, the multifunctional composition of the present disclosure is well suited for preserving all different types of personal care products.

During the above testing, it was noticed that the multifunctional composition of the present disclosure, in some embodiments, had a tendency to change the color of the product. In particular, the product assumed a light pink color. The light pink color may provide various advantages for some of the personal care products.

Through testing, it was determined that the color change may be controlled by selecting the emollients used in the personal care product. In addition, controlling the pH of the personal care product may also affect any color differences. In particular, lowering the pH may prevent a color change. The presence of a triglyceride in the personal care product may cause a color change to occur, such as a capric/caprylic triglyceride. In view of the above, the composition of the present disclosure can also be used to change the color of the product when desired or the personal care product may be formulated so that the composition has no significant color change effect.

Example No. 2

In this example, two compositions made according to the present disclosure were tested for minimum inhibitory concentration (MIC) as described in Example No. 1. In this example, the first sample tested was the same as Sample No. 4 described above in Example No. 1. The second sample (Sample No. 8) was identical to Sample No. 4 except 1,3 propanediol was replaced with 1,5 pentanediol. In certain applications, pentanediol displays greater compatibility with the other ingredients. The following results were obtained:

| | Sample No. | |
|---|---|---|
| | No. 4 | No. 8 |
| | Prepared Concentration | |
| Organism | 32.7% MIC (ppm) | 32.2% MIC (ppm) |
| Staphylococcus aureus | 20,400 | 20,100 |
| Bacillus subtilis | 10,200 | 10,100 |
| Staphylococcus epidermidis | 10,200 | 10,100 |
| Pseudomonas aeruginosa | 10,200 | 20,100 |
| Escherichia coli | 10,200 | 10,100 |
| Enterococcus hirae | 20,400 | 20,100 |
| Candida albicans | 2,550 | 2,520 |
| Saccharomyces cerevisiae | 5,110 | 5,030 |
| Staphylococcus haemolyticus | 5,110 | 10,100 |
| Bacillus licheniformis | 5,110 | 2,520 |
| Corynebacterium xerosis | 5,110 | 5,030 |
| Corynebacterium minutissimum | 5,110 | 5,030 |
| Propionibacterium acnes | 2,550 | 2,520 |
| Aspergillus brasiliensis | 2,550 | 2,520 |
| Tricophyton mentagrophytes | 639 | 629 |
| Aureobasidium pullulans | 2,550 | 2,520 |
| Malassezia furfur | 1,280 | 1,260 |
| Trichoderma virens | 2,550 | 2,520 |

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A personal care product for topical application to a user's skin or hair comprising:
   a base composition; and
   a multi-functional composition, the multi-functional composition being present in the personal care product in an amount from 0.1% to 5% by weight, the multi-functional composition comprising
      an organic acid comprising an aliphatic acid in an amount from 0.5% to 5% by weight based on the total weight of the multi-functional composition,
      a diol in an amount from 40% to 77.5% by weight based on the total weight of the multi-functional composition, and
      an active compound having the following formula:

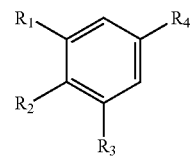

wherein:
      $R_1$ and $R_2$ are H or OH;
      $R_3$ comprises H, OH, or $OR_5$;
      $R_4$ comprises $R_6COOR_7$; $COOR_7$; or $R_8C{=}O$;
      $R_5$ is an alkyl group;
      $R_6$ is an alkyl or alkenyl group;
      $R_7$ is H, an alkyl group or an alkenyl group; and
      $R_8$ is H, an alkyl group or an alkenyl group.

2. A personal care product as defined in claim 1, wherein the multi-functional composition further comprises a dispersant.

3. A personal care product as defined in claim 1, wherein the active compound comprises:

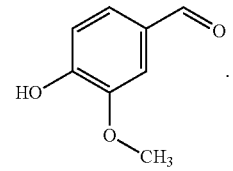

4. A personal care product as defined in claim 1, wherein the active compound comprises:

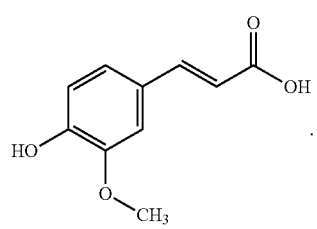

5. A personal care product as defined in claim 1, wherein the active compound comprises:

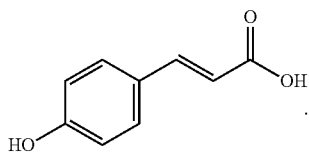 [SMILES: O=C(O)/C=C/c1ccc(O)cc1]

6. A personal care product as defined in claim 1, wherein the active compound comprises:

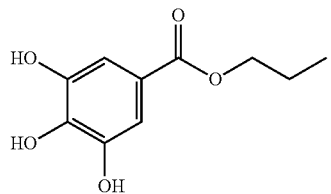

7. A personal care product as defined in claim 1, wherein the active compound comprises:

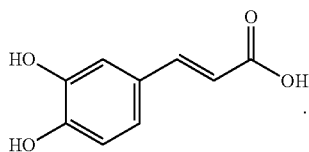 [SMILES: O=C(O)/C=C/c1ccc(O)c(O)c1]

8. A personal care product as defined in claim 1, wherein the active compound comprises:

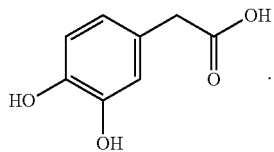 [SMILES: O=C(O)Cc1ccc(O)c(O)c1]

9. A personal care product as defined in claim 1, wherein the active compound comprises:

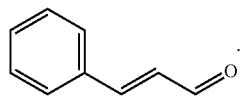

10. A personal care product as defined in claim 2, wherein
the active compound is present in the multi-functional composition in an amount from about 15% to about 30% by weight;
the dispersant is present in the multi-functional composition in an amount from about 5% to about 40% by weight; and
the diol is present in the multi-functional composition in an amount from about 40% to about 60% by weight;
wherein the weight is based on the total weight of the multi-functional composition.

11. A personal care product as defined in claim 1, wherein the active compound and the organic acid are made entirely from natural ingredients.

12. A personal care product as defined in claim 1, wherein the active compound and the organic acid are present in the multi-functional composition at a ratio of from about 3:1 to about 20:1.

13. A personal care product as defined in claim 1, wherein the active compound is present in the personal care product in an amount of from about 500 ppm to about 5,000 ppm.

14. A personal care product as defined in claim 1, wherein the personal care product comprises a shampoo, a face cream, a makeup remover, a conditioner, a skin lotion, or a mascara.

15. A personal care product as defined in claim 1, wherein the organic acid comprises an organic acid having a carbon chain length of from about 3 carbon atoms to about 18 carbon atoms.

16. A personal care product as defined in claim 1, wherein the organic acid comprises octanoic acid.

17. A personal care product as defined in claim 2, wherein the dispersant comprises polyglyceryl oleate, polyglyceryl caprylate, polyglyceryl caprate, or mixtures thereof.

18. A multi-functional composition comprising an organic acid comprising an aliphatic acid in an amount from 0.5% to 5% by weight, a diol in an amount from 40% to 77.5% by weight, and an active compound having the following formula:

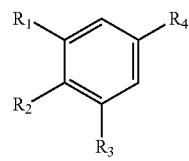

wherein:

$R_1$ and $R_2$ are H or OH;

$R_3$ comprises H, OH, or $OR_5$;

$R_4$ comprises $R_6COOR_7$; $COOR_7$; or $R_8C=O$;

$R_5$ is an alkyl group;

$R_6$ is an alkyl or alkenyl group;

$R_7$ is H, an alkyl group or an alkenyl group; and $R_8$ is H, an alkyl group or an alkenyl group, wherein the active compound and the organic acid are present in the multi-functional composition at a ratio of from 3:1 to 20:1, and wherein the weight is based on the total weight of the multi-functional composition.

19. A multi-functional composition as defined in claim 18, wherein the active compound comprises:

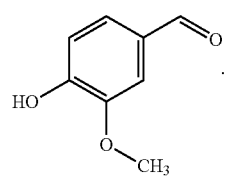

20. A multi-functional composition as defined in claim 18, wherein the active compound comprises:

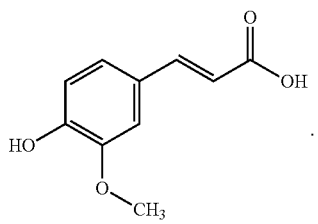

21. A multi-functional composition as defined in claim 18, wherein the active compound comprises:

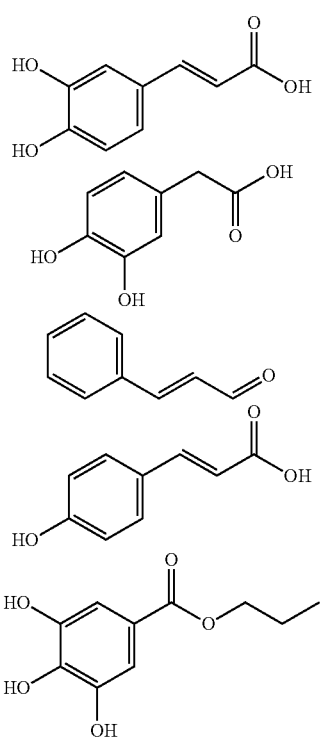

or mixtures thereof.

22. A multi-functional composition as defined in claim 18, wherein the active compound is present in the multi-functional composition in an amount from about 15% to about 30% by weight;

the diol is present in the multi-functional composition in an amount from about 40% to about 60% by weight; and further comprising a dispersant, the dispersant is present in the multi-functional composition in an amount from about 5% to about 40% by weight, wherein the weight is based on the total weight of the multi-functional composition.

23. A multi-functional composition comprising an organic acid comprising an aliphatic acid having a chain length of from 3 carbon atoms to 18 carbon atoms and being present in an amount from 0.5% to 5% by weight, a diol in an amount from 40% to 60% by weight, a polyglyceryl ester in an amount from 15% to 35% by weight, and an active compound in an amount from 15% to 30% by weight wherein the active compound has the following formula:

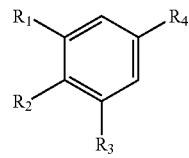

wherein:
$R_1$ and $R_2$ are H or OH;
$R_3$ comprises H, OH, or $OR_5$;
$R_4$ comprises $R_6COOR_7$; $COOR_7$; or $R_8C=O$;
$R_5$ is an alkyl group;
$R_6$ is an alkyl or alkenyl group;
$R_7$ is H, an alkyl group or an alkenyl group; and
$R_8$ is H, an alkyl group or an alkenyl group,
wherein the weight is based on the total weight of the multi-functional composition.

24. A personal care product comprising the multi-functional composition according to claim 23.

25. A personal care product comprising the multi-functional composition according to claim 18.

* * * * *